US008088146B2

(12) United States Patent  
Wert et al.

(10) Patent No.: US 8,088,146 B2
(45) Date of Patent: Jan. 3, 2012

(54) HIGH-STRENGTH SUTURE

(75) Inventors: Zachary D. Wert, Providence, RI (US);
David T. Faris, Fall River, MA (US);
Frances Warfield, Columbia, CT (US);
Debra Masso, East Haven, CT (US)

(73) Assignee: Teleflex Medical Incorporated, Limerick, PA (US)

( * ) Notice: Subject to any disclaimer, the term of this patent is extended or adjusted under 35 U.S.C. 154(b) by 913 days.

(21) Appl. No.: 10/867,400

(22) Filed: Jun. 14, 2004

(65) Prior Publication Data

US 2005/0277985 A1   Dec. 15, 2005

(51) Int. Cl.
*A61B 17/04* (2006.01)

(52) U.S. Cl. ........................................ 606/228

(58) Field of Classification Search .......... 606/144–150, 606/224–233; 623/13.11–13.16, 13.19, 13.2; 57/243, 903; 87/9; 428/36.1, 36.2, 36.3
See application file for complete search history.

(56) References Cited

U.S. PATENT DOCUMENTS 3,918,455 A * 11/1975 Coplan ........................... 606/225
3,949,755 A    4/1976 Vauquois .................... 128/335.5
4,008,303 A * 2/1977 Glick et al. ..................... 264/78
4,034,763 A * 7/1977 Frazier .......................... 606/226
4,043,344 A    8/1977 Landi et al. ................ 128/335.5
4,047,533 A    9/1977 Perciacante et al. ....... 128/335.5

(Continued)

FOREIGN PATENT DOCUMENTS

EP      1 530 976 A1    5/2005

(Continued)

OTHER PUBLICATIONS

Zimmer et al., "Influence of Knot Configuration and Tying Technique on the Mechanical Performance of Sutures", The Journal of Emergency Medicine, vol. 9, pp. 107-113, 1991 (month unknown).

*Primary Examiner* — Darwin Erezo
*Assistant Examiner* — Alexander Orkin
(74) *Attorney, Agent, or Firm* — Baker & Hostetler LLP

(57) ABSTRACT

A surgical suture is made of an elongate, hollow braid of high strength fibers. The braid defines an elongate, longitudinally-extending, central chamber that is open and without any core material extending therein so that, when a surgeon's knot is tied with the suture, the cross-sectional shape of the braid collapses upon itself and is reduced in size in response to pressures experienced when the knot is tightened thereby producing a low profile knot that resists slippage. Preferably, the braid is of a size corresponding to a USP size 5-0 to USP size 7 suture and has one or more, preferably a pair, of color contrasting monofilaments woven therein to enhance suture visibility. Methods of making a flattened suture and of utilizing the high strength suture to maintain body tissues in an engaged position to promote healing are also provided.

12 Claims, 4 Drawing Sheets

U.S. PATENT DOCUMENTS

| | | | |
|---|---|---|---|
| 4,510,934 A * | 4/1985 | Batra | 606/231 |
| 4,546,769 A | 10/1985 | Planck et al. | 128/335.5 |
| 4,790,850 A | 12/1988 | Dunn et al. | 623/13 |
| 4,792,336 A | 12/1988 | Hlavacek et al. | 623/13 |
| 4,946,467 A | 8/1990 | Ohi et al. | 606/228 |
| 5,019,093 A | 5/1991 | Kaplan et al. | 606/228 |
| 5,318,575 A | 6/1994 | Chesterfield et al. | 606/151 |
| 5,456,722 A * | 10/1995 | McLeod et al. | 128/898 |
| 5,540,703 A | 7/1996 | Barker, Jr. et al. | 606/139 |
| 5,628,756 A | 5/1997 | Barker, Jr. et al. | 606/139 |
| 6,045,571 A | 4/2000 | Hill et al. | 606/228 |
| 6,716,234 B2 | 4/2004 | Grafton et al. | 606/228 |
| 2003/0050667 A1 | 3/2003 | Grafton et al. | 606/228 |
| 2003/0139775 A1 | 7/2003 | Grafton | 606/228 |
| 2004/0162579 A1 * | 8/2004 | Foerster | 606/228 |
| 2005/0048281 A1 * | 3/2005 | Royer et al. | 428/364 |
| 2005/0119696 A1 * | 6/2005 | Walters et al. | 606/228 |

FOREIGN PATENT DOCUMENTS

| | | |
|---|---|---|
| EP | 1 541 181 A1 | 6/2005 |
| WO | WO 03/022161 A1 | 3/2003 |

* cited by examiner

"PRIOR ART"

y dim = x dim or Round y dim = x dim or Round y dim < x dimension by design = flat ures are discussed in the article by Zimmer et al. titled
HIGH-STRENGTH SUTURE

BRIEF SUMMARY OF THE INVENTION

This invention relates to a surgical suture, and more particularly, to a high-strength surgical suture providing improved knot tie down characteristics that enable surgeons to form low profile knots having superior knot security.

Sutures are elongate implant devices used to maintain body tissues together to promote natural healing and/or to compress blood vessels to stop bleeding. Sutures are typically knotted to hold divided wound edges together, and the mechanical performance of surgeons' knots has an effect on proper wound healing. If a suture and/or knot fails, it should fail due to breakage, not due to knot slippage. Examples of tests for determining the mechanical performance of knotted sut"Influence of Knot Configuration and Tying Technique on the Mechanical Performance of Sutures" published in The Journal of Emergency Medicine, Volume 9, pages 107-113, 1991.

Sutures are manufactured in various sizes, typically according to standards established by the United States Pharmacopeia (USP). Suture size is typically determined by the diameter or gauge of the round cross-section of the suture. See Table 1 provided below.

TABLE 1

| USP-Size | Metric Gauge No. | Diameter, Min-Max (mm) |
|---|---|---|
| 12-0 | 0.01 | 0.001-0.009 |
| 11-0 | 0.1 | 0.010-0.019 |
| 10-0 | 0.2 | 0.020-0.029 |
| 9-0 | 0.3 | 0.030-0.039 |
| 8-0 | 0.4 | 0.040-0.049 |
| 7-0 | 0.5 | 0.050-0.069 |
| 6-0 | 0.7 | 0.070-0.099 |
| 5-0 | 1.0 | 0.100-0.149 |
| 4-0 | 1.5 | 0.150-0.199 |
| 3-0 | 2.0 | 0.200-0.249 |
| 2-0 | 3.0 | 0.300-0.339 |
| 0 | 3.5 | 0.350-0.399 |
| 1 | 4.0 | 0.400-0.499 |
| 2 | 5.0 | 0.500-0.599 |
| 3 and 4 | 6.0 | 0.600-0.699 |
| 5 | 7.0 | 0.700-0.799 |
| 6 | 8.0 | 0.800-0.899 |
| 7 | 9.0 | 0.900-0.999 |
| 8 | 10.0 | 1.000-1.099 |
| 9 | 11.0 | 1.100-1.199 |
| 10 | 12.0 | 1.200-1.299 |

Surgical sutures, particularly those of USP size 5-0 and greater, have been constructed having a core of fibers extending within an outer braided cover or sheathing of fibers. See prior art suture 100 illustrated in FIG. 1. Suture 100 has an outer braided sheathing of fibers 102 surrounding a twisted core of fibers 104 and has a round cross section (ie., the x dimension equals the y dimension as illustrated in FIG. 1). Examples of surgical sutures having cores are also provided by U.S. Pat. No. 4,946,467 issued to Ohi et al., U.S. Pat. No. 4,546,769 issued to Planck et al., and U.S. Pat. No. 6,045,571 issued to Hill et al. The core fibers are used to increase the strength of the suture and to provide the suture with a rounded cross-section. Needles used with sutures typically have a round cross-section and make round holes, and it has been believed desirable to make the cross-section of sutures as round as possible to fill the round holes to reduce bleeding. Thus, cores enable the roundness of the cross-section of the suture to be maintained during use. However, such sutures have experienced problems relating to the different elongation to break between the core and cover materials and problems relating to the core popping through the cover.

Surgical sutures have been made of high strength materials. For example, U.S. Pat. No. 5,318,575 issued to Chesterfield et al. discloses so-called "high-strength" fibers to manufacture spiroid and hollow braided surgical sutures having cores. An example of a high strength fiber is ultra-high molecular weight, extended-chain polyethylene high-tenacity fiber sold under the tradename "SPECTRA". U.S. Pat. No. 4,790,850 issued to Dunn et al., U.S. Pat. No. 4,792,336 issued to Hlavacek et al., U.S. Pat. Nos. 5,628,756 and 5,540,703 issued to Barker, Jr. et al. and U.S. Pat. No. 5,456,722 issued to McLeod et al. disclose high-strength, ultra-high molecular weight polyethylene fibers in relatively large diameter surgical cables used as prosthetic ligaments, tendon implants, and the like. Also see U.S. Pat. No. 6,716,234 B2 issued to Grafton et al. and U.S. Patent Application Publication Nos. U.S. 2003/0050667 A1 and U.S. 2003/0139775 A1 which disclose high-strength sutures made in part of ultra-high molecular weight polyethylene fibers, such as those sold under the trademarks "SPECTRA" and "DYNEEMA".

Fibers of contrasting colors have been utilized in surgical sutures to enhance suture visibility, and suture handling properties have been improved with coatings including various lubricants and the like. For example, U.S. Pat. No. 3,949,755 issued to Vauquois discloses a braided suture having fibers of contrasting colors, and U.S. Pat. No. 4,043,344 issued to Landi et al., U.S. Pat. No. 4,047,533 issued to Perciaccante et al., and U.S. Pat. No. 5,019,093 issued to Kaplan et al. disclose various coatings utilized on sutures.

While the aforementioned sutures may be satisfactory for their intended purposes, there is a need for an improved surgical suture that is made of high strength fibers and that possesses improved knot-tying and knot-security properties. To this end, a lubricious, multi-filament suture, permitting the construction of a secure knot having a low profile and improved knot security, is desired. In addition, the suture should have enhanced visibility and handling characteristics.

The invention addresses the foregoing objects by providing a surgical suture made of an elongate woven braid of fibers that include ultra-high molecular weight polyethylene fibers. The braid of fibers is hollow and is without any core material extending therein. The absence of a core enables the cross-sectional shape of the braid of fibers to become altered in response to pressures exerted thereon when the suture is knotted so that a knot having a low profile is formed. Preferably, the braid of fibers is of a size corresponding to a suture with the range from about USP sizes 5-0 to 7 (ie., the suture has a diameter in the range from about 0.100 to 0.999 mm).

According to another aspect of the present invention a method is provided for maintaining body tissues in an engaged position to promote healing. A suture is used to stitch the body tissues together and at least one knot is tied with the suture to hold the body tissues together for at least a predetermined period of time that is required for proper healing. The suture is an elongate woven braid of fibers including ultra-high molecular weight polyethylene fibers, and the braid of fibers is hollow without a core material extending therein. During the tying step, the cross-sectional shape of the braid of fibers changes in response to pressures experienced during knotting thereby providing a knot having a low profile. Preferably, the suture has an initial size, before knotting, corresponding to a USP size 5-0 to USP size 7 suture (ie., a diameter between about 0.100 to 0.999 mm).

DETAILED DESCRIPTION

The invention relates to a surgical suture made of an elongate, hollow braid of high strength fibers and a method of making the suture. In addition, the invention relates to a method of utilizing the high strength suture to maintain body tissues in an engaged position to promote healing.

Figure 1:
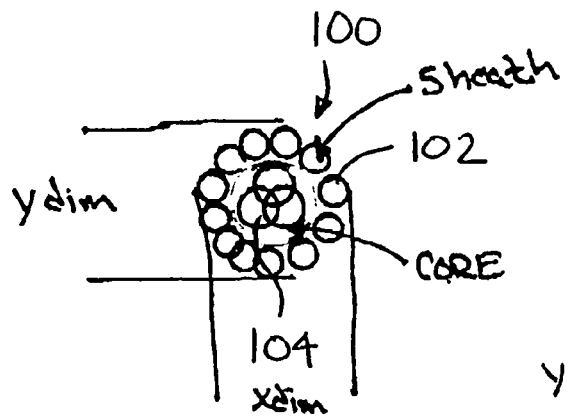
FIG. 1 is a cross-sectional view of a suture having a core according to the prior art.

Typically, surgical sutures are made to have round cross-sections of sizes corresponding to those identified on the size chart provided above in Table 1. Sutures made of a hollow braid of fibers that correspond to a USP size 5-0 to a USP size 7 suture include a reinforcing core material extending within the braid. See FIG. 1. The core material fills the central open void within the braid so that a desired round cross-section is maintained throughout use of the suture as discussed above. For examples of such sutures, see the disclosures provided by U.S. Pat. No. 5,318,575 issued to Chesterfield et al., U.S. Pat. No. 6,045,571 issued to Hill et al., and U.S. Pat. No. 6,716,234 B2 issued to Grafton et al. and U.S. Patent Application Publication Nos. U.S. 2003/0050667 A1 and U.S. 2003/0139775 A1. Sutures smaller than USP size 5-0 sutures are too small to have central open voids and have been made without a core material simply because adequate space for a core material is not available. U.S. Pat. Nos. 5,628,756 and 5,540,703 issued to Barker, Jr. et al. and U.S. Pat. No. 5,456,722 issued to McLeod et al. disclose large braided surgical cables having diameters of at least 1 to 3 mm. These braids are made of 9 to 13 picks per inch and from large denier ends (ie., minimum 650 denier) on an eight carrier braider providing a total minimum denier of 5200 denier (ie., 8×650). Thus, such large braids also provide no void or open space in which a core material can be extended.

Figure 2:
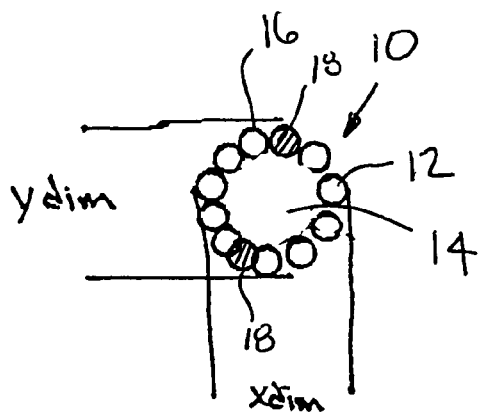
FIG. 2 is a cross-sectional view of a suture without a core according to the present invention.
Figure 3:
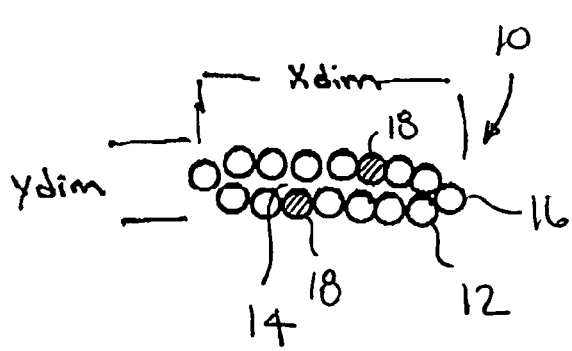
FIG. 3 is a cross-sectional view of a flattened suture without a core according to the present invention.

As best illustrated in FIGS. 2 and 3, the suture 10 according to the present invention is a hollow braid of fibers 12 of a size within a range of USP size 5-0 to USP size 7 (ie., has a diameter between about 0.1 to about 0.999 mm as measured when in a round condition as illustrated in FIG. 2). Unlike prior art sutures of like sizes, the suture 10 is coreless without any core material extending within the hollow braid 12. Thus, the braid 12 defines an elongate, longitudinally-extending, central chamber 14 that is without a core material extending therein. FIG. 2 illustrates a cross-section of suture 10 when disposed in a circular configuration. However, the suture 10 according to the present invention can also be provided in an oval, relatively flat, or tape-like configuration as illustrated in FIG. 3 since the braid 12 is coreless and can collapse upon itself. For purposes of this application, the size of suture 10 corresponds to diameter measurements taken when suture 10 is disposed in a substantially circular cross-sectional configuration, such as shown in FIG. 2.

The coreless, hollow-braided suture 10 provides improved knot-tying and knot-security capabilities. When a knot is tied with suture 10, the cross-sectional shape and size of suture 10 at the knot changes and becomes reduced since the pressure exerted during the formation of the knot causes the suture 10 to collapse upon itself at the knot site. This reduces the length, width, volume and mass of the knot providing it with a profile that is significantly less than that of a similarly sized prior art suture having a core. Thus, the presence of the open central chamber 14 and the absence of any core material therein for the above referenced range of suture size permits the ready formation of low profile knots that remain secure without slippage for an extended period of time. This results in significant advantages relative to knots tied with prior art braided sutures that have a core material, since the presence of a core material limits the ability of a prior art suture to collapse upon itself during knot tying and tightening actions.

Preferably, the braid 12 is made of high strength fibers 16, such as ultra-high molecular weight polyethylene fibers, to compensate for the absence of a core material. For example, braid 12 can be made entirely (100%) of ultra-high molecular weight polyethylene fibers, or alternatively, can include one or more strands of a different fiber/filament. Preferably, the high strength fibers 16 in the braid 12 form at least 75%, or 90%, of the total fibers of the braid 12, so that a suture 10 having high strength is provided despite the absence of a core material.

In a preferred embodiment, the suture 10 includes one or more, preferably two, strands of a color contrasting monofilament 18 to enhance suture visibility during surgery. The ultra-high molecular weight polyethylene fibers 16 are typically white or translucent. Thus, the suture 10 preferably includes a strand or stands of a monofilament 18 that is of a highly-visible contrasting color and that is woven in the braid 12 with the ultra-high molecular weight polyethylene fibers 16. As an example, the monofilament 18 can be a deep blue color. Alternatively, strands of other colors can be utilized. Preferably, the color-contrasting monofilament 18 is a color-extruded monofilament of polypropylene or polydioxanone. To this end, preferably a colorant or pigment is compounded into a resin before the resin is extruded to form a color-extruded monofilament. Thus, preferably the monofilament 18 is not subjected to a post-formation dyeing step as typically required for polyester and nylon materials.

By way of example, the braid of suture 10 can include 8, 16, 24, or 32 ends braided together at approximately 50-70 pics per inch. The various numbers of ends used are for the purpose of changing the resultant size of the finished braid while holding the denier constant. Preferably, the suture 10 includes only ultra-high molecular weight polyethylene fibers 16 and one or more, preferably a pair, of color-contrasting monofilaments 18 of a color-extruded monofilament of polypropylene or polydioxanone. As a specific example, the braid 12 can include sixteen ends braided together with fourteen ends being ultra-high molecular weight polyethylene fibers 16 and a pair of ends being color-contrasting polypropylene monofilaments 18 located at opposed positions within the braid. Preferably the color contrasting monofilaments 18 comprise no more than 25% of the total fibers of the braid 12. In addition, preferably the suture 10 is of a size within a range of USP size 5-0 to USP size 7 (ie., has a diameter of at least about 0.1 mm and less than 1.0 mm), and optionally, the suture 10 can be coated with wax, silicone, silicone rubber, PTFE, PBA, ethyl cellulose or like coating to improve handling, lubricity of the braid, abrasion resistance, and like characteristics.

A method of maintaining body tissues in an engaged position to promote healing is also provided by the present invention. To this end, a USP size 5-0 to USP size 7 suture is utilized to stitch body tissues together and a surgeon's knot is tied with the suture to hold the body tissues together for at least a predetermined period of healing time. As discussed above, the suture 10 is an elongate woven braid of fibers including ultra-high molecular weight polyethylene fibers, and the braid of fibers is hollow and has an elongate, longitudinally-extending, central chamber that is open and without a core material extending therein. Thus, during knot tying, the braid 12 at the site of the knot is reduced in size, diameter, and shape in response to pressures experienced during tying thereby producing a knot having a reduced mass, volume, and profile.

EXAMPLES

An example of a coreless braided suture according to the invention and tests with respect to the dimensions and security of knots formed with the suture are provided below and are contrasted with sutures having cores according to the prior art. General information concerning braid construction is disclosed by U.S. Pat. No. 6,045,571 issued to Hill et al., and general information concerning suture knot construction and tests of mechanical performance of knots are disclosed in the article of Zimmer et al. titled "Influence of Knot Configuration and Tying Technique on the Mechanical Performance of Sutures" published in 1991 in The Journal of Emergency Medicine, Volume 9, pages 107-113. The disclosures of both of these references are incorporated herein by reference.

For testing purposes, a USP size 2 braided suture according to the invention was made with a sixteen-carrier New England Butt braider No. 1. Each carrier held 110 denier DYNEEMA ultra high molecular weight polyethylene fiber, and the braider was equipped with a cross shaft gear of 82 and a lower change gear of 24. The gears provide an expected pick count of 62 picks per inch (PPI). The braided suture according to the present invention was flattened by being passed over and under two rollers before transition to a smaller step roll (1.185 inch) and five passes to a roller before final take up on an iron head. The rollers can be made of metal or ceramic, and the geometry of the rollers to each other serve to flatten the braid. See FIG. 3 for an example of the shape of the flattened braid.

Tables 2 and 3, provided below, show the effects on suture diameter of flattening the braided suture of the invention. To this end, Table 2 provides diameter measurements in mils of fifteen samples of the suture according to the invention that were not subjected to the above referenced flattening procedures, and Table 3 provides diameter measurements in mils of fifteen samples of the suture according to the invention that were subjected to the above referenced flattening procedures. Low diameters, high diameters and average diameters are measured for each sample and overall averages are listed below the last line of the tables.

TABLE 2

NORMAL BRAID (see FIG. 2)

| Low Diameter (MIL) | High Diameter (MIL) | Average Diameter (MIL) |
| --- | --- | --- |
| 22.9 | 24.4 | 23.7 |
| 23.0 | 24.3 | 23.7 |
| 22.7 | 24.3 | 23.5 |
| 23.0 | 24.3 | 23.7 |
| 23.4 | 24.7 | 24.1 |
| 23.1 | 24.5 | 23.8 |
| 23.1 | 24.7 | 23.9 |
| 22.7 | 24.5 | 23.6 |
| 22.9 | 24.4 | 23.7 |
| 23.2 | 24.7 | 24.0 |
| 23.5 | 25.0 | 24.3 |
| 23.1 | 24.6 | 23.9 |
| 23.1 | 24.6 | 23.9 |
| 23.1 | 24.7 | 23.9 |
| 22.9 | 24.8 | 23.9 |
| Ave.: 23.0 | 24.6 | 23.8 |

TABLE 3

FLATTENED BRAID (see FIG. 3)

| Low Diameter (MIL) | High Diameter (MIL) | Average Diameter (MIL) |
| --- | --- | --- |
| 20.0 | 26.3 | 23.2 |
| 21.2 | 23.2 | 22.2 |
| 20.0 | 26.7 | 23.4 |
| 20.8 | 27.2 | 24.0 |
| 20.4 | 27.3 | 23.9 |
| 19.8 | 27.1 | 23.5 |
| 20.2 | 27.0 | 23.6 |
| 20.6 | 25.1 | 22.9 |
| 20.7 | 27.4 | 24.1 |
| 19.9 | 26.2 | 23.1 |
| 20.5 | 22.9 | 21.7 |
| 20.2 | 27.8 | 24.0 |
| 20.3 | 27.4 | 23.9 |
| 20.1 | 27.6 | 23.9 |
| 20.0 | 27.9 | 24.0 |
| Ave.: 20.3 | 26.5 | 23.4 |

For testing purposes, a USP size 2 braided suture having a core according to the prior art was also made with a sixteen-carrier New England Butt braider No. 1. Each carrier held 110 denier DYNEEMA ultra high molecular weight polyethylene fiber. The braid was formed as a cover over a center core of a three ply of 220 denier DYNEEMA ultra high molecular weight polyethylene fiber. The braider was equipped with a cross shaft gear of 82, a lower change gear of 24, and a small step roll (1.185 inch). The gears provide an expected pick count of 62 picks per inch (PPI).

Various tests were run with the above referenced suture according to the invention and the above referenced prior art suture having a core. In addition, different types of knots were tested for the sutures. As will be discussed in greater detail, the tests show that the coreless suture according the invention can be used to create knots of lower profile and of better security than the comparative prior art sutures.

Figure 4:
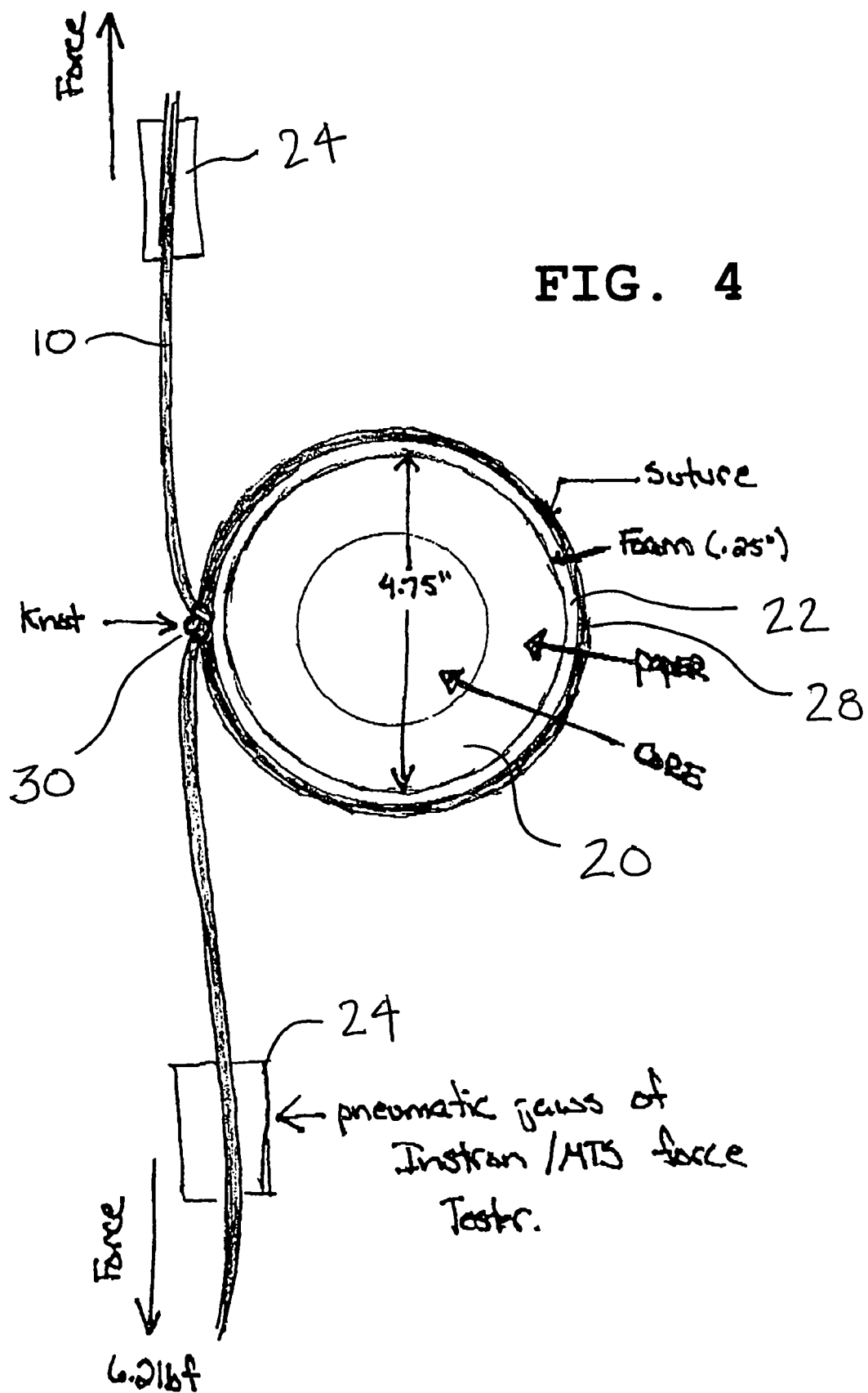
FIG. 4-6 are views of a suture knot testing assembly.
Figure 5:
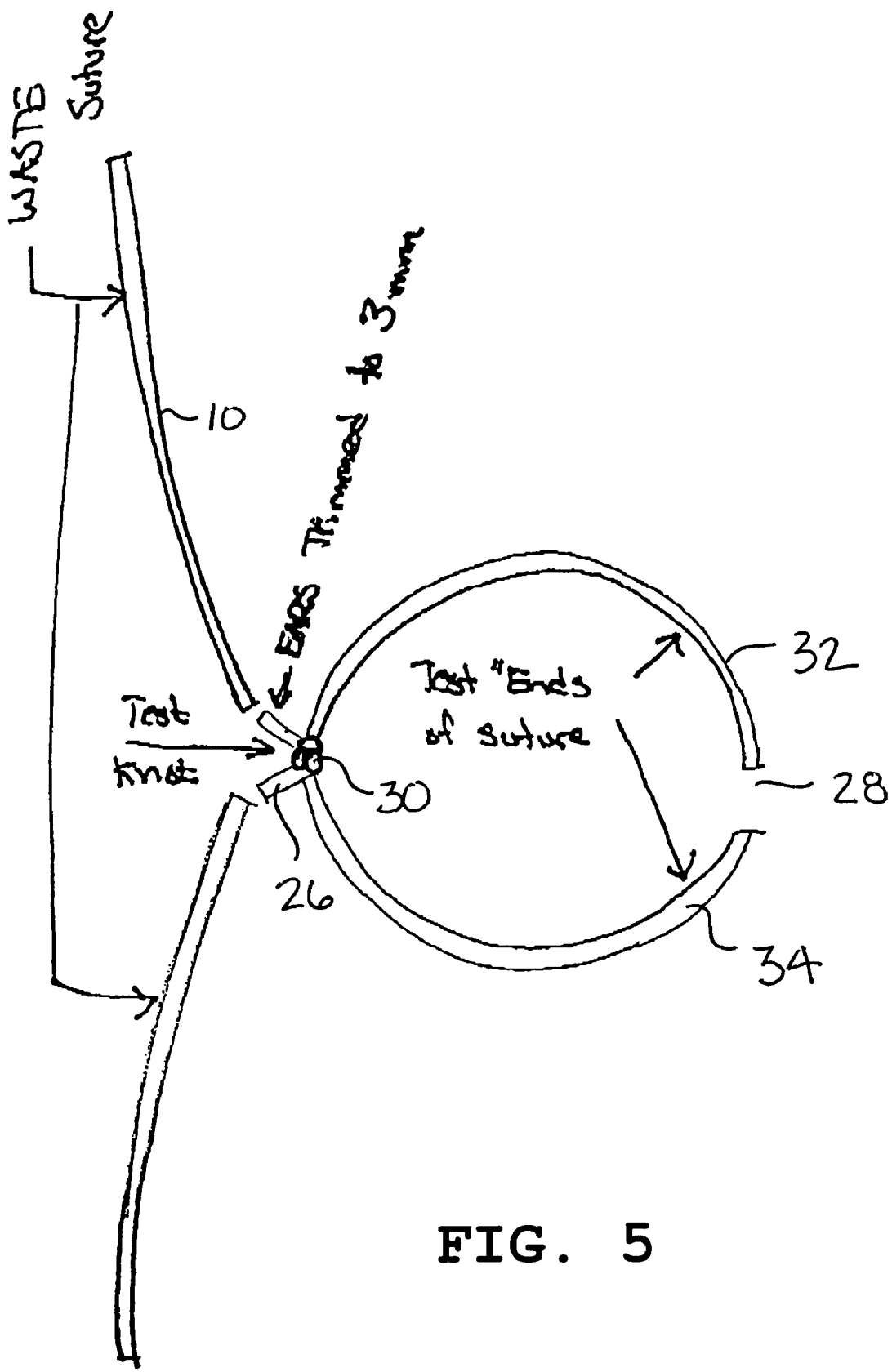
Figure 6:
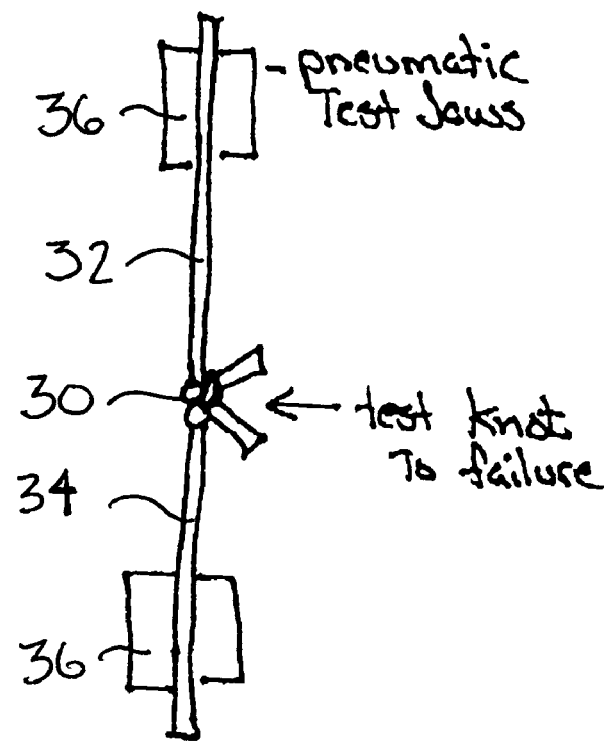
Figure 7:
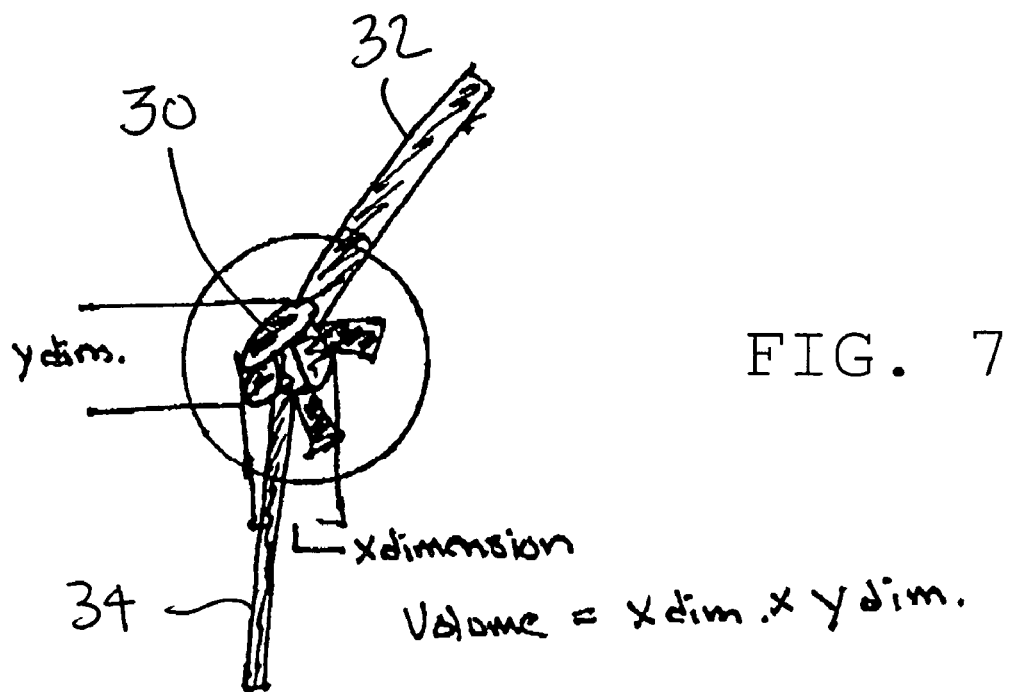
FIG. 7 is a view of a knot showing the dimensions measured to determine the volume of the knot.

The test utilized a MTS Reliance RT/5 test frame with a 500 N load cell installed on the MTS Reliance RT/5 test frame. For each knot 30 to be evaluated, a suture was tied around a 4.75 inch roll of paper 20 covered with a 0.25 inch layer of foam rubber 22 as illustrated in FIG. 4. All knots tested included a square knot followed by one or more square or granny throws. Beginning with the second throw of each knot, equal tension was applied to each throw of the knot configuration by the pneumatic jaws 24 of the MTS Reliance RT/5 test frame with an extension rate of 500 mm/min to a final tension of 6.2 lbf, which represents 80% of the USP knot pull tensile strength requirement of the suture. Thereafter, the ears 26 of the knot 30 were trimmed to approximately 3 mm, and the suture was removed from the roll 20 by cutting the suture at the midpoint 28 opposite the knot 30 at the back of the roll 20. See FIG. 5. The knot dimensions of the removed suture was then measured and its knot security tested on an Instron 3300 tensile strength instrument. See FIGS. 6 and 7.

The dimensions of each knot 30 was measured on a Nikon Measurescope MM-11 microscope. The knot 30 was placed on the plate of the microscope with suture ends 32 and 34 extended, and weights were used to hold the knot in a fixed position. The width and length of the knot was measured in inches with the microscope along x-coordinate and y-coordinate directions. See FIG. 7.

Patient side knot security was tested for each knot 30 by placing the suture ends, 32 and 34, of the knot between fiber grips 36 of the Instron tensile strength instrument. See FIG. 6. The tensile strength was tested, and it was observed wether or not the knot slipped (S) or broke (B). The peak load observed before breakage or slippage was recorded as well as the mode of separation, ie., S or B.

The results of the tests are shown in the following Tables. Table 4 provides the results of tests on the present invention, Table 5 provides the results of tests on the above described comparative suture having a core, and Table 6 provides the results of tests on a poly-blend suture having a core made according to U.S. Pat. No. 6,716,234 B2 issued to Grafton et al. The tested knots include a two throw square knot with additional square throws. The standard convention for a square throw "=" is used. For example, a knot type identified as "1=1=1=1" is a two throw square knot ("1=1") with two additional square throws ("=1=1"), and a knot type identified as "1=1=1=1" is a two throw square knot ("1=1") with three additional square throws ("=1=1=1"). Table 7 provides a summary of the knot dimension and knot security measurements listed in detail in Tables 4-6.

TABLE 4

Knot Test Data for Suture of Invention

| Knot Type | Trial No. | Security | Break/Slip (lb) | Height (in) | Volume (in$^3$) × 10$^3$ |
|---|---|---|---|---|---|
| 1 = 1 = 1 = 1 | 1 | Break | 29.7 | 0.1200 | 0.652 |
| | 2 | Slip | 25.5 | 0.1344 | 0.599 |
| | 3 | Break | 29.5 | 0.1114 | 0.516 |
| | 4 | Slip | 25.7 | 0.1279 | 0.724 |
| | 5 | Break | 29.4 | 0.1014 | 0.639 |
| | 6 | Slip | 20.9 | 0.1509 | 0.591 |
| | 7 | Slip | 18.7 | 0.1152 | 0.786 |
| | 8 | Slip | 23.7 | 0.1527 | 0.615 |
| | 9 | Slip | 25.3 | 0.1235 | 0.709 |
| | 10 | Slip | 23.8 | 0.1100 | 0.801 |
| | Ave. | 30% Break | 25.2 | 0.1247 | 0.663 |
| 1 = 1 = 1 = 1 = 1 | 1 | Break | 31.2 | 0.1573 | 0.922 |
| | 2 | Break | 29.8 | 0.1898 | 1.067 |
| | 3 | Break | 29.3 | 0.1643 | 1.232 |
| | 4 | Slip | 28.0 | 0.1238 | 1.277 |
| | 5 | Break | 29.3 | 0.1572 | 1.091 |
| | 6 | Break | 30.1 | 0.1717 | 1.179 |
| | 7 | Break | 26.7 | 0.1432 | 1.207 |
| | 8 | Break | 29.7 | 0.1512 | 1.847 |
| | 9 | Break | 29.7 | 0.1720 | 1.308 |
| | 10 | Break | 27.9 | 0.1552 | 0.966 |
| | Ave. | 90% Break | 29.2 | 0.1586 | 1.209 |

TABLE 5

Knot Test Data for Comparative Suture having a Core

| Knot Type | Trial No. | Security | Break/Slip (lb) | Height (in) | Volume (in$^3$) × 10$^3$ |
|---|---|---|---|---|---|
| 1 = 1 = 1 = 1 | 1 | Slip | 26.4 | 0.1479 | 0.979 |
| | 2 | Slip | 27.4 | 0.1378 | 1.232 |
| | 3 | Slip | 24.9 | 0.1374 | 1.017 |
| | 4 | Slip | 25.6 | 0.1177 | 0.897 |
| | 5 | Slip | 24.8 | 0.1230 | 0.911 |
| | 6 | Slip | 23.9 | 0.1485 | 1.323 |
| | 7 | Slip | 24.4 | 0.1678 | 1.323 |
| | 8 | Slip | 25.0 | 0.1728 | 1.030 |
| | 9 | Slip | 21.7 | 0.1672 | 1.097 |
| | 10 | Slip | 21.6 | 0.1947 | 1.949 |
| | Ave. | 0% Break | 24.6 | 0.1515 | 1.176 |
| 1 = 1 = 1 = 1 = 1 | 1 | Slip | 30.3 | 0.2244 | 1.331 |
| | 2 | Break | 34.5 | 0.2044 | 2.266 |
| | 3 | Break | 35.3 | 0.2216 | 2.008 |
| | 4 | Break | 34.1 | 0.1631 | 1.082 |
| | 5 | Break | 37.2 | 0.1759 | 0.856 |
| | 6 | Break | 33.9 | 0.2313 | 1.207 |
| | 7 | Slip | 35.2 | 0.1979 | 1.220 |
| | 8 | Break | 35.1 | 0.1701 | 1.203 |

TABLE 5-continued

Knot Test Data for Comparative Suture having a Core

| Knot Type | Trial No. | Security | Break/Slip (lb) | Height (in) | Volume (in$^3$) × 10$^3$ |
|---|---|---|---|---|---|
| | 9 | Slip | 31.6 | 0.2245 | 0.847 |
| | 10 | Break | 34.8 | 0.1774 | 0.978 |
| | Ave. | 70% Break | 34.2 | 0.1991 | 1.300 |

TABLE 6

Knot Test Data for suture made according to U.S. Pat. No. 6,716,234 B2

| Knot Type | Trial No. | Security | Break/Slip (lb) | Height (in) | Volume (in$^3$) × 10$^3$ |
|---|---|---|---|---|---|
| 1 = 1 = 1 = 1 = 1 | 1 | Slip | 24.3 | 0.1900 | 1.249 |
| | 2 | Break | 27.5 | 0.1869 | 0.546 |
| | 3 | Break | 26.7 | 0.1826 | 0.733 |
| | 4 | Slip | 21.5 | 0.1896 | 1.274 |
| | 5 | Slip | 19.6 | 0.2045 | 0.751 |
| | 6 | Slip | 26.8 | 0.1512 | 1.240 |
| | 7 | Slip | 22.3 | 0.1891 | 0.813 |
| | 8 | Break | 30.8 | 0.1776 | 1.046 |
| | 9 | Slip | 25.7 | 0.1772 | 1.056 |
| | 10 | Slip | 18.7 | 0.1919 | 1.205 |
| | Ave. | 30% Break | 24.4 | 0.1841 | 0.991 |

TABLE 7

Knot Dimension and Security Summary

Two Throw Square Knot with Additional Square Throws

| | Knot: 1 = 1 = 1 = 1 | | | Knot: 1 = 1 = 1 = 1 = 1 | | |
|---|---|---|---|---|---|---|
| Suture | Height (in) | Volume (in$^3$) × 10$^3$ | Security | Height (in) | Volume (in$^3$) × 10$^3$ | Security |
| Invention (coreless) | 0.1247 | 0.663 | 30% | 0.1586 | 1.209 | 90% |
| Comparative Example (w/core) | 0.1515 | 1.176 | 0% | 0.1991 | 1.300 | 70% |
| Poly-blend with core | NA | NA | NA | 0.1841 | 0.991 | 30% |

The results of tests for knots that include a two throw square knot with one or more additional granny throws are provided in Tables 8-9. To this end, the standard convention for a granny throw "x" is used. For example, a knot type identified as "1=1x1" is a two throw square knot ("1=1") with an additional granny throw ("x1"), a knot type identified as "1=1x1x1" is a two throw square knot ("1=1") with two additional granny throws ("x1x1"), and a knot type identified as "1=1x1x1x1" is a two throw square knot ("1=1") with three additional granny throws ("x1x1x1"). Table 8 provides the results of tests on the present invention, Table 9 provides the results of tests on the above described comparative suture having a core, and Table 10 provides a summary of the knot dimension and knot security measurements listed in detail in Tables 8 and 9.

TABLE 8

Knot Test Data for Suture of Invention

| Knot Type | Trial No. | Security | Break/Slip (lb) | Height (in) | Volume (in³) × 10³ |
|---|---|---|---|---|---|
| 1 = 1 × 1 | 1 | Slip | 12.8 | NA | NA |
| | 2 | Slip | 13.3 | NA | NA |
| | 3 | Slip | 13.1 | NA | NA |
| | 4 | Slip | 13.5 | NA | NA |
| | 5 | Slip | 13.0 | NA | NA |
| | 6 | Slip | 12.3 | NA | NA |
| | 7 | Slip | 15.4 | NA | NA |
| | 8 | Slip | 13.8 | NA | NA |
| | 9 | Slip | 14.0 | NA | NA |
| | 10 | Slip | 11.9 | NA | NA |
| | Ave. | 0% Break | 13.3 | | |
| 1 = 1 × 1 × 1 | 1 | Slip | 21.5 | 0.1363 | 0.808 |
| | 2 | Slip | 22.3 | 0.1023 | 0.799 |
| | 3 | Break | 26.2 | 0.1425 | 1.248 |
| | 4 | Slip | 20.7 | 0.1125 | 1.048 |
| | 5 | Slip | 22.5 | 0.1405 | 0.495 |
| | 6 | Slip | 23.9 | 0.1578 | 0.927 |
| | 7 | Slip | 24.4 | 0.1316 | 0.945 |
| | 8 | Slip | 26.3 | 0.1318 | 0.952 |
| | 9 | Slip | 18.3 | 0.1425 | 1.057 |
| | 10 | Slip | 14.7 | 0.1267 | 1.105 |
| | Ave. | 10% Break | 22.1 | 0.1325 | 0.939 |
| 1 = 1 × 1 × 1 × 1 | 1 | Break | 30.7 | 0.1514 | 0.890 |
| | 2 | Break | 28.6 | 0.1657 | 0.954 |
| | 3 | Break | 30.0 | 0.1935 | 0.944 |
| | 4 | Slip | 26.9 | 0.2179 | 1.140 |
| | 5 | Break | 30.5 | 0.1470 | 1.086 |
| | 6 | Break | 27.8 | 0.1563 | 0.955 |
| | 7 | Break | 26.3 | 0.1537 | 1.316 |
| | 8 | Break | 27.8 | 0.1492 | 1.377 |
| | 9 | Break | 29.6 | 0.1889 | 1.136 |
| | 10 | Break | 30.3 | 0.1506 | 1.675 |
| | Ave. | 90% Break | 28.9 | 0.1674 | 1.147 |

TABLE 9

Knot Test Data for Comparative Example with core

| Knot Type | Trial No. | Security | Break/Slip (lb) | Height (in) | Volume (in³) × 10³ |
|---|---|---|---|---|---|
| 1 = 1 × 1 | 1 | Slip | 14.9 | NA | NA |
| | 2 | Slip | 9.1 | NA | NA |
| | 3 | Slip | 15.2 | NA | NA |
| | 4 | Slip | 14.1 | NA | NA |
| | 5 | Slip | 13.2 | NA | NA |
| | 6 | Slip | 14.1 | NA | NA |
| | 7 | Slip | 7.1 | NA | NA |
| | 8 | Slip | 13.7 | NA | NA |
| | 9 | Slip | 13.0 | NA | NA |
| | 10 | Slip | 14.8 | NA | NA |
| | Ave. | 0% Break | 12.9 | | |
| 1 = 1 × 1 × 1 | 1 | Slip | 24.6 | 0.1566 | 1.582 |
| | 2 | Slip | 26.0 | 0.1315 | 1.136 |
| | 3 | Slip | 25.4 | 0.1463 | 1.533 |
| | 4 | Slip | 25.4 | 0.1366 | 1.073 |
| | 5 | Slip | 27.6 | 0.1245 | 1.443 |
| | 6 | Slip | 22.1 | 0.1606 | 1.591 |
| | 7 | Slip | 24.6 | 0.1503 | 1.505 |
| | 8 | Slip | 22.9 | 0.1751 | 1.378 |
| | 9 | Slip | 25.1 | 0.1391 | 1.826 |
| | 10 | Slip | 21.3 | 0.1197 | 1.381 |
| | Ave. | 0% Break | 24.5 | 0.1440 | 1.445 |
| 1 = 1 × 1 × 1 × 1 | 1 | Slip | 36.0 | 0.1739 | 1.698 |
| | 2 | Break | 35.0 | 0.1991 | 1.370 |
| | 3 | Slip | 36.0 | 0.2065 | 1.485 |
| | 4 | Break | 35.1 | 0.1699 | 1.867 |
| | 5 | Slip | 29.0 | 0.1906 | 2.656 |
| | 6 | Break | 34.7 | 0.1963 | 2.467 |
| | 7 | Slip | 30.2 | 0.1920 | 2.490 |
| | 8 | Slip | 32.4 | 0.1763 | 2.427 |
| | 9 | Slip | 28.0 | 0.2035 | 3.356 |
| | 10 | Break | 32.1 | 0.2015 | 2.634 |
| | Ave. | 40% Break | 32.9 | 0.1910 | 2.245 |

TABLE 10

Knot Dimension and Security Summary

Two Throw Square Knot with Additional Granny Throws

| | Knot: 1 = 1 × 1 × 1 | | | Knot: 1 = 1 × 1 × 1 × 1 | | |
|---|---|---|---|---|---|---|
| Suture | Height (in) | Volume (in³) × 10³ | Security | Height (in) | Volume (in³) × 10³ | Security |
| Invention (coreless) | 0.1325 | 0.939 | 10% | 0.1674 | 1.147 | 90% |
| Comparative Example (w/core) | 0.1440 | 1.445 | 0% | 0.1910 | 2.245 | 40% |

As indicated by the results in the above referenced Tables, the coreless braided suture of the invention permits surgeons to construct knots that snug down to a lower profile (ie., height) than that permitted by the comparative sutures having cores. In addition, the results demonstrate that the coreless braided suture of the invention provides better knot security (ie., less slippage).

While preferred sutures and methods of use have been described, various modifications, alterations, and changes may be made without departing from the spirit and scope of the invention as defined in the appended claims.

The invention claimed is:

1. A surgical suture comprising an elongate woven braid of fibers including ultra-high molecular weight polyethylene fibers, said braid of fibers being hollow and defining an elongate, longitudinally-extending, open central chamber without a core material extending therein, said chamber having a cross-sectional diameter that is substantially larger than a diameter of the fibers and being sufficiently large to enable a cross-sectional shape of said braid of fibers to collapse in response to pressures experienced when the suture is knotted to permit the formation of knots that resist slippage, wherein greater than 90% of said fibers of said braid are said ultra-high molecular weight polyethylene fibers,
   wherein said braid is of a size within a range corresponding to a USP size 5-0 to USP size 7 suture, and
   wherein said suture has a diameter in the range between 0.100 mm to 0.999 mm, and
   wherein said suture has a substantially circular round cross-sectional configuration which collapses in response to pressures experienced when the suture is knotted.

2. A surgical suture according to claim 1, wherein said diameter is at least 0.100 mm to about 0.799 mm, and said braid is of a size within a range corresponding to a USP size 5-0 to USP size 5 suture.

3. A surgical suture according to claim 1, wherein said braid of fibers includes at least one strand of a color-contrasting monofilament of a color different from that of said ultra-high molecular weight polyethylene fibers.

4. A surgical suture according to claim 3, wherein said color-contrasting monofilament is a color-extruded monofilament of polypropylene or polydioxanone and is woven with said plurality of ultra-high molecular weight polyethylene fibers to form said braid of fibers.

5. A surgical suture according to claim 1, wherein a denier of each of said fibers is no greater than about 110 denier.

6. A surgical suture according to claim 5, wherein said braid of fibers includes at least one strand of a color-contrasting monofilament of a color different from that of said ultra-high molecular weight polyethylene fibers.

7. A surgical suture according to claim 6, wherein said color-contrasting monofilament is a color-extruded monofilament of polypropylene or polydioxanone.

8. A surgical suture according to claim 7, wherein said braid of fibers includes a pair of opposed strands of said color-contrasting monofilament with a remainder of said fibers in said braid consisting of said ultra-high molecular weight polyethylene fibers.

9. A surgical suture comprising an elongate woven braid of fibers corresponding to a size within a range of USP size 5-0 to USP size 7 suture, said braid having 8 to 32 fibers braided together at about 50 to about 70 picks per inch, greater than 90% of said fibers of said braid being ultra-high molecular weight polyethylene fiber, said braid of fibers being hollow and defining an elongate, longitudinally-extending, open central chamber without a core material extending therein, said chamber having a cross-sectional diameter that is substantially larger than a diameter of the fibers and said chamber enabling a cross sectional shape of said braid to change in response to pressures experienced when the suture is knotted to permit the formation of knots that resist slippage, and wherein said suture has a diameter in the range from 0.100 mm to 0.999 mm, and wherein said suture has a substantially circular round cross-sectional configuration which collapses in response to pressures experienced when the suture is knotted, and wherein a total denier of said suture is between about 880 to 3520 denier.

10. A surgical suture according to claim 9, wherein said braid of fibers includes at least one strand of a color-contrasting monofilament of a color different from that of said ultra-high molecular weight polyethylene fibers.

11. A surgical suture according to claim 10, wherein said color-contrasting monofilament is a color-extruded monofilament of polypropylene or polydioxanone.

12. A method for maintaining body tissues in an engaged manner to promote healing comprising the steps of utilizing a USP size 5-0 to USP size 7 suture having a diameter in the range from 0.100 mm to 0.999 mm to stitch said body tissues together and tying a knot with said suture to hold said body tissues together for at least a predetermined period of time, said suture being an elongate woven braid of fibers including ultra-high molecular weight polyethylene fibers, said braid of fibers being hollow and having an elongate, longitudinally-extending, open central chamber without a core material extending therein during the step of stitching said body tissues together, and so that, during said tying step, a cross sectional shape of said braid changes in response to pressures experienced during knotting so that said knot is a knot that resists slippage, wherein the open central chamber has a cross-sectional diameter that is substantially larger than a diameter of the fibers, and wherein greater than 90% of said fibers of said braid are said ultra-high molecular weight polyethylene fibers.

* * * * *